US011041193B2

(12) United States Patent
Rasmussen et al.

(10) Patent No.: US 11,041,193 B2
(45) Date of Patent: Jun. 22, 2021

(54) MULTIPLE AMPLIFICATION CYCLE DETECTION

(71) Applicant: BioFire Diagnostics, LLC, Salt Lake City, UT (US)

(72) Inventors: Randy P. Rasmussen, Salt Lake City, UT (US); Robert John Crisp, Salt Lake City, UT (US); Andrew Clinton Hemmert, Murray, UT (US); Elizabeth Barker Campbell, Orem, UT (US); Thomas Charles Robbins, Salt Lake City, UT (US); David J. Eyre, Salt Lake City, UT (US)

(73) Assignee: BioFire Diagnostics, LLC, Salt Lake City, UT (US)

( * ) Notice: Subject to any disclaimer, the term of this patent is extended or adjusted under 35 U.S.C. 154(b) by 378 days.

(21) Appl. No.: 16/037,948

(22) Filed: Jul. 17, 2018

(65) Prior Publication Data

US 2018/0320220 A1 Nov. 8, 2018

Related U.S. Application Data

(62) Division of application No. 14/425,588, filed as application No. PCT/US2013/058752 on Sep. 9, 2013, now Pat. No. 10,053,726.

(60) Provisional application No. 61/699,103, filed on Sep. 10, 2012.

(51) Int. Cl.
*C12P 19/34* (2006.01)
*C12Q 1/686* (2018.01)
*C12Q 1/6851* (2018.01)
*C12Q 1/689* (2018.01)
*C12Q 1/70* (2006.01)

(52) U.S. Cl.
CPC ............ *C12Q 1/686* (2013.01); *C12Q 1/689* (2013.01); *C12Q 1/6851* (2013.01); *C12Q 1/705* (2013.01)

(58) Field of Classification Search
CPC .................................................. C12Q 1/686
See application file for complete search history.

(56) References Cited

U.S. PATENT DOCUMENTS

| 6,387,621 | B1 | 5/2002 | Wittwer | |
|---|---|---|---|---|
| 6,730,501 | B2 | 5/2004 | Eyre et al. | |
| 7,373,253 | B2 | 5/2008 | Eyre | |
| 7,413,852 | B2 | 8/2008 | Balch | |
| 8,394,608 | B2 | 3/2013 | Ririe et al. | |
| 2003/0077611 | A1* | 4/2003 | Slepnev | C12Q 1/6809 435/6.14 |
| 2004/0014117 | A1* | 1/2004 | Slepnev | C12Q 1/686 435/6.11 |
| 2004/0166513 | A1* | 8/2004 | Slepnev | C12Q 1/6851 435/6.14 |
| 2009/0136951 | A1* | 5/2009 | Hart | C12Q 1/6851 435/6.12 |
| 2009/0258414 | A1 | 10/2009 | Wittwer et al. | |
| 2009/0306230 | A1 | 12/2009 | Semikhodskii et al. | |
| 2010/0056383 | A1 | 3/2010 | Ririe et al. | |
| 2010/0297656 | A1 | 11/2010 | Wittwer et al. | |
| 2011/0076674 | A1 | 3/2011 | Blaschke-Bonkowsky et al. | |
| 2011/0238323 | A1 | 9/2011 | Robbins et al. | |
| 2012/0301875 | A1 | 11/2012 | Wittwer et al. | |

FOREIGN PATENT DOCUMENTS

| CA | 2786916 | 7/2011 |
|---|---|---|
| CN | 101405411 | 4/2009 |
| JP | 2007097492 | 4/2007 |
| JP | 2010004781 | 1/2010 |
| JP | 2010207220 | 9/2010 |
| WO | 2008140568 | 11/2008 |
| WO | 2009156916 | 12/2009 |
| WO | 2013074391 | 5/2013 |

OTHER PUBLICATIONS

Extended European Search Report corresponding to European Patent Application No. 13835180.4 (20 pages) (dated Jul. 18, 2016).
Extended European Search Report corresponding to European Patent Application No. 18179752.3 (12 pages) (dated Jul. 31, 2018).
Favaro et al. "A Multi-Target Real-Time PCR Assay for Rapid Identification of Meningitis-Associated Microorganisms" Molecular Biotechnology, 53:74-79 (2013).
Heid et al. "Real Time Quantitative PCR" Genome Research 6(10):986-994 (1996).
Human herpesvirus-6 and human herpesvirus-7 (HHV-6, HHV-7), Virus, vol. 60 No. 2, pp. 221-236 (2010).
International Preliminary Report on Patentability corresponding to International Patent Application No. PCT/US2013/058752 (dated Mar. 10, 2015).
International Search Report and the Written Opinion of the International Searching Authority corresponding to International Patent Application No. PCT/US2013/055752 (dated Feb. 7, 2014).
Introduction of Medical Biological Detection and Protection Technology, edited by Pan Xin, Beijing, Military Medical Science Press, pp. 42-45 (Jul. 2011).
"LightCycler Operator's Manual" Version 3.5 (186 pages) (Oct. 2000).
Nitsche et al. "Different Real-Time PCR Formats Compared for the Quantitative Detection of Human Cytomegalovirus DNA" Clinical Chemistry 45(11):1932-1937 (1999).
Office Action corresponding to Chinese Patent Application No. 201380046847.7 (18 pages) (dated May 3, 2018).

(Continued)

*Primary Examiner* — Kenneth R Horlick
(74) *Attorney, Agent, or Firm* — Myers Bigel, P.A.

(57) ABSTRACT

Methods and devices are provided for simultaneously amplifying a plurality of sample wells for a predetermined amount of amplification, detecting whether amplification has occurred in a first set of the wells, amplifying for an additional amount of amplification and detecting whether amplification has occurred in a second set of the wells. Methods are also provided for analyzing a target nucleic acid sequence using melt curves that were generated in a plurality of amplification cycles.

15 Claims, 10 Drawing Sheets

(56) References Cited

OTHER PUBLICATIONS

Partial Supplementary European Search Report corresponding to European Patent Application No. 13835180.4 (10 pages) (dated Mar. 7, 2016).
QuantiFast Probe PCR, Protocol and Troubleshooting, QIAGEN (20 pages) (Jan. 2007).
Ririe et al. "Product Differentiation by Analysis of DNA Melting Curves during the Polymerase Chain Reaction" Analytical Biochemistry 245:154-160 (1997).
Vallier et al. "RNAI in the cereal weevil *Sitophilus* spp: Systemic gene knockdown in the bacteriome tissue" BMC Bioteohnoloay 9(1):1-7 (2009).
Velusamy et al. "An overview of foodborne pathogen detection: In the perspective of biosensors" Biotechnology Advances 28:232-254 (2008).
Wittwer et al. "Real-Time Multiplex PCR Assays" Methods 25:430-442 (2001).
Yang Dali et at. "DNA Amplification Technology and Medical Applications" Shandong Science and Technology Press pp. 81-82 (Nov. 1992).
Operator Manual: SmartCycler II (248 pages) (1999-2005).

\* cited by examiner

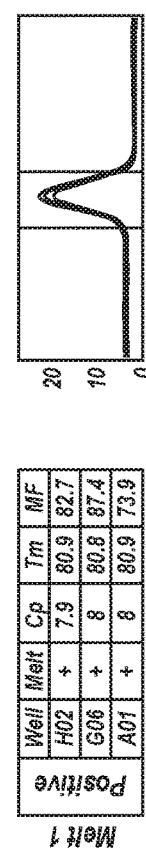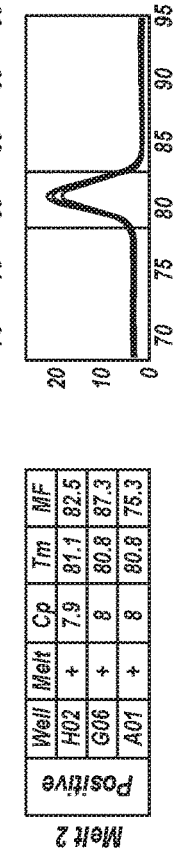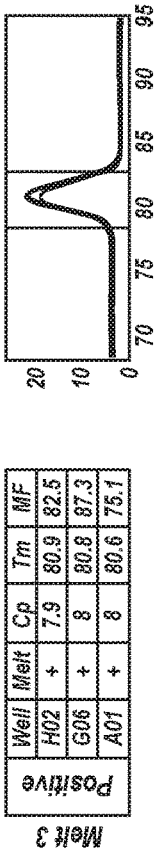
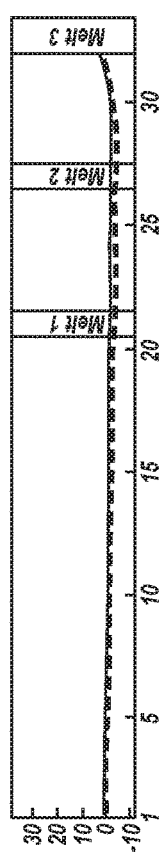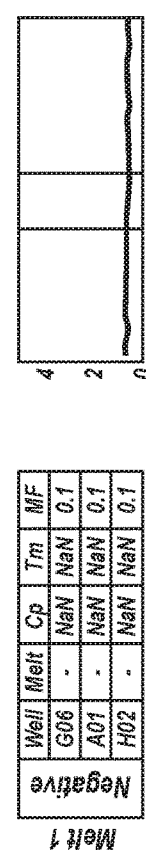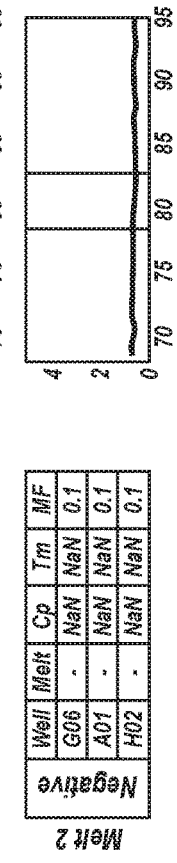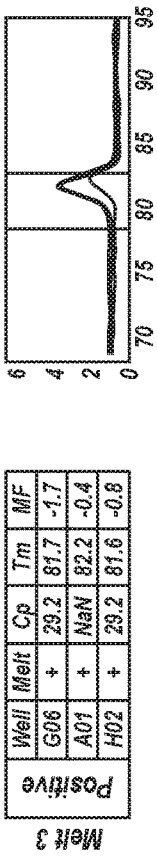
FIG. 2A
FIG. 2B

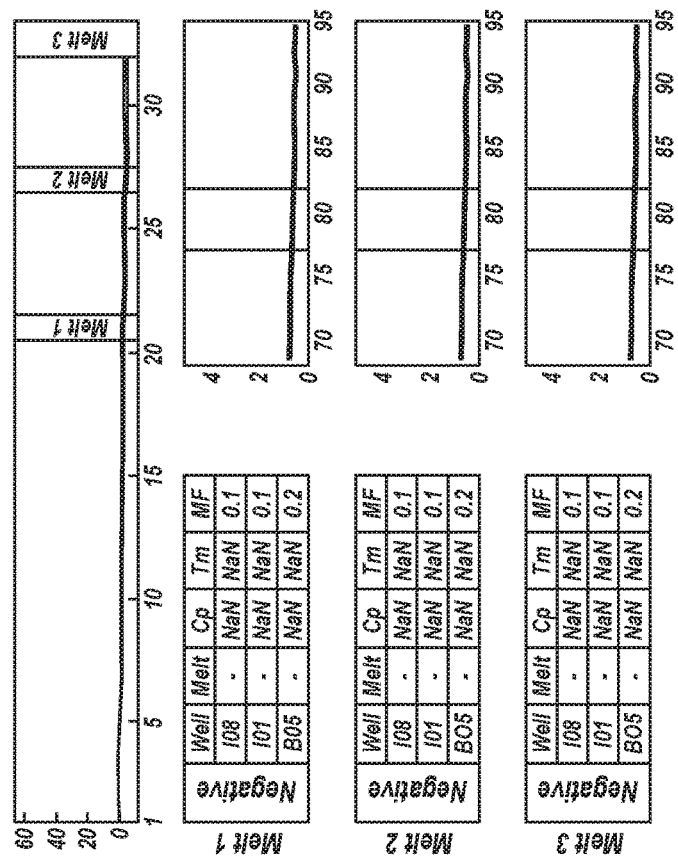
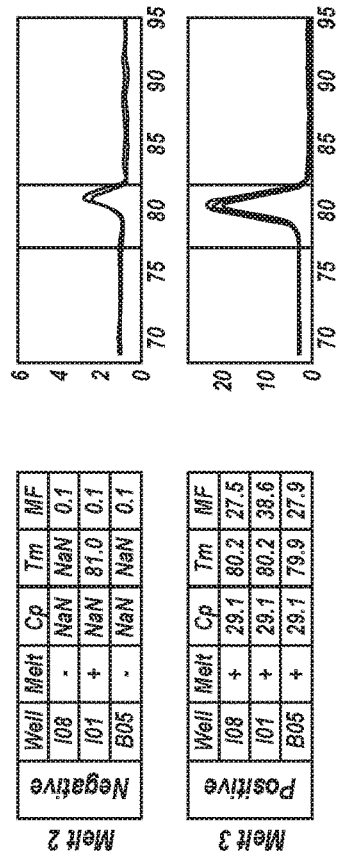
FIG. 3A
FIG. 3B

MULTIPLE AMPLIFICATION CYCLE DETECTION

CROSS-REFERENCE TO RELATED APPLICATIONS

This application is a divisional application of U.S. application Ser. No. 14/425,588, filed Mar. 3, 2015, which issued as U.S. Pat. No. 10,053,726 on Aug. 21, 2018, which is a 35 USC § 371 national phase application of International Application Serial No. PCT/US2013/058752, filed Sep. 9, 2013, which claims the benefit of and priority to U.S. Provisional Application No. 61/699,103, filed on Sep. 10, 2012, entitled "Multiple Amplification Cycle Detection," the entire contents of each of which are incorporated herein by reference.

GOVERNMENT INTEREST

This invention was made with government support under Grant No. 1U01 AI082184 awarded by National Institutes of Health. The government has certain rights in the invention.

BACKGROUND OF THE INVENTION

In the United States, Canada, and Western Europe infectious disease accounts for approximately 7% of human mortality, while in developing regions infectious disease accounts for over 40% of human mortality. Infectious diseases lead to a variety of clinical manifestations. Among common overt manifestations are fever, pneumonia, meningitis, diarrhea, and diarrhea containing blood. While the physical manifestations suggest some pathogens and eliminate others as the etiological agent, a variety of potential causative agents remain, and clear diagnosis often requires a variety of assays to be performed. Traditional microbiology techniques for diagnosing pathogens can take days or weeks, often delaying a proper course of treatment.

In recent years, the polymerase chain reaction (PCR) has become a method of choice for rapid diagnosis of infectious agents. PCR can be a rapid, sensitive, and specific tool to diagnose infectious disease. A challenge to using PCR as a primary means of diagnosis is the variety of possible causative organisms and the low levels of organism present in some pathological specimens. It is often impractical to run large panels of PCR assays, one for each possible causative organism, most of which are expected to be negative. The problem is exacerbated when pathogen nucleic acid is at low concentration and requires a large volume of sample to gather adequate reaction templates. In some cases, there is inadequate sample to assay for all possible etiological agents. A solution is to run "multiplex PCR" wherein the sample is concurrently assayed for multiple targets in a single reaction. While multiplex PCR has proven to be valuable in some systems, shortcomings exist concerning robustness of high level multiplex reactions and difficulties for clear analysis of multiple products. To solve these problems, the assay may be subsequently divided into multiple secondary PCRs. Nesting secondary reactions within the primary product often increases robustness. However, this further handling can be expensive and may lead to contamination or other problems.

The FilmArray® (BioFire Diagnostics, Inc., Salt Lake City, Utah) is a user friendly, highly multiplexed PCR system developed for the diagnostic market. The single sample instrument accepts a diagnostic "pouch" that integrates sample preparation and nested multiplex PCR. Integrated sample preparation provides ease-of-use, while the highly multiplexed PCR provides both the sensitivity of PCR and the ability to test for up to 30 different organisms simultaneously. This system is well suited to pathogen identification where a number of different pathogens all manifest similar clinical symptoms. Current available diagnostic panels include a respiratory panel for upper respiratory infections and a blood culture panel for blood stream infections. Other panels are in development.

Many of the organisms that are targeted in FilmArray panels, as well as in panels for use with other instruments, are commonly present in the environment. While such environmental contamination tends to be present in concentrations that are significantly below that of a clinically relevant sample, it can be difficult to distinguish between environmental contamination and clinical infection. Also, certain individuals have latent viral infections through chromosomal integration, wherein the chromosomally integrated viral DNA may or may not be responsible for the clinical symptoms. It would be desirable to have methods for determining whether a positive result is due to a clinically relevant infection or due to another source of nucleic acid.

SUMMARY OF THE INVENTION

The present disclosure relates to methods for simultaneously amplifying a number of targets, while distinguishing between clinically relevant amplification and amplification from other sources such as from background contamination, cross-reactivity in the amplification reaction, or chromosomal integration.

In one aspect of the present invention methods and devices for identifying which of a plurality of target nucleic acids is in a sample are disclosed. The disclosed methods comprise providing a plurality of sample wells, each sample well provided with primers for amplifying a locus from a different one of the plurality of target nucleic acid sequence, providing a portion of the sample into each of the plurality of sample wells, simultaneously subjecting the plurality of sample wells to amplification conditions through a number of amplification cycles, detecting whether amplification has occurred in each of a first set of the plurality of sample wells, simultaneously subjecting the plurality of sample wells to amplification conditions through a number of additional amplification cycles, detecting whether amplification has occurred in each of a second set of the plurality of sample wells, and identifying the target nucleic acid present in the sample by identifying the corresponding sample well in which amplification has occurred.

In another illustrative embodiment, methods are provided for distinguishing between chromosomal integration and clinically-relevant infection in a sample, illustratively comprising providing a sample well provided with the sample and primers for amplifying a target nucleic acid sequence from the sample, subjecting the sample well to amplification conditions through a number of amplification cycles, detecting whether amplification has occurred in the sample well, subjecting the sample well to amplification conditions through a number of additional amplification cycles, and detecting whether amplification has occurred in the sample well. In certain illustrative examples, a positive call in the first detecting step may be indicative of chromosomal integration, and a negative call in the first detecting step with a positive call in the second detecting step may be indicative of a clinically-relevant infection.

In yet another illustrative embodiment, methods for analyzing a target nucleic acid in a sample are provided comprising
(a) providing a sample well comprising therein the sample and primers for amplifying the target nucleic acid,
(b) subjecting the sample well to amplification conditions through a at least one amplification cycle,
(c) generating a melt curve of the amplified target nucleic acid, and
(d) repeating steps (b) and (c).
These methods may further include determining a value for the melt curve, and determining a Cp by identifying the amplification cycle in which the value for the melt curve exceeds a predetermined value. In illustrative examples, the value may be determined by peak height or peak area of a negative derivative of the melt curve.

In still another example, methods for analyzing a target nucleic acid in a sample are provided comprising
(a) providing a sample well including the sample, primers for amplifying the target nucleic acid, a control nucleic acid, primers for amplifying the control nucleic acid, and a dsDNA binding dye,
(b) subjecting the sample well to amplification conditions through a plurality of amplification cycles,
(c) generating a melt curve of the amplified target nucleic acid and amplified control nucleic acid,
(d) determining a value for the amplified target nucleic acid, and
(e) repeating steps (b), (c), and (d).
Such illustrative methods may also include the step of generating a corrected amplification curve for the target nucleic acid using the values determined in step (d), and plotting corrected amplification curves, or determining relative concentrations between the two nucleic acids.

Reaction vessels and devices are also provided herein. Additional features of the present invention will become apparent to those skilled in the art upon consideration of the following detailed description of preferred embodiments exemplifying the best mode of carrying out the invention as presently perceived.

BRIEF DESCRIPTION OF THE FIGURES

FIGS. 2A-B show amplification and melt curves after three different cycles for *A. baumannii*. FIG. 2A shows data for a false positive and FIG. 2B shows data for a true positive.

FIGS. 3A-B show amplification and melt curves after three different cycles for *C. tropicalis*. FIG. 3A shows data for a negative sample and FIG. 3B shows data for a positive sample.

FIG. 4A shows data for a negative sample and FIG. 4B shows data for a positive sample.

DETAILED DESCRIPTION

Figure 1:
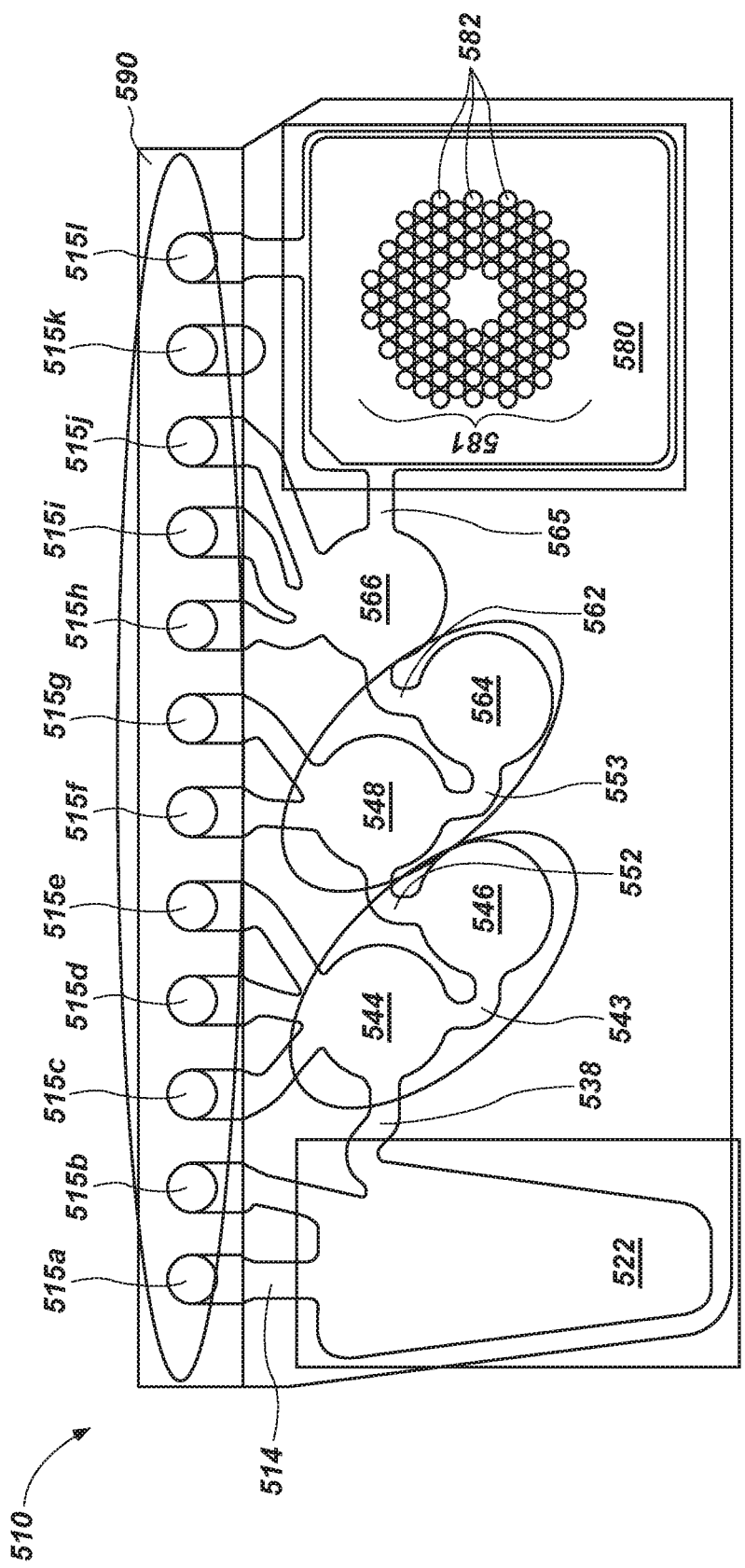
FIG. 1 shows an illustrative pouch for use in one embodiment in this disclosure.

As used herein, the terms "a," "an," and "the" are defined to mean one or more and include the plural unless the context is inappropriate. Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g. a polypeptide or nucleic acid); or a solution containing a non-naturally occurring nucleic acid, which is assayed as described herein. A sample may also be any body fluid or excretion (for example, but not limited to, blood, urine, stool, saliva, tears, bile, cerebrospinal fluid) that contains cells, cell components, or nucleic acids.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

By "probe," "primer," or "oligonucleotide" is meant a single-stranded DNA or RNA molecule of defined sequence that can base-pair to a second DNA or RNA molecule that contains a complementary sequence (the "target"). The stability of the resulting hybrid depends upon the length, GC content, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes may be used to detect dsDNA. It is understood that a "primer" is specifically configured to be extended by a polymerase, whereas a "probe" or "oligonucleotide" may or may not be so configured.

By "dsDNA binding dyes" is meant dyes that fluoresce differentially when bound to double-stranded DNA than when bound to single-stranded DNA or free in solution, usually by fluorescing more strongly. While reference is made to dsDNA binding dyes, it is understood that any suitable dye may be used herein, with some non-limiting illustrative dyes described in U.S. Pat. No. 7,387,887, herein incorporated by reference. Other signal producing substances may be used for detecting nucleic acid amplification and melting, illustratively enzymes, antibodies, etc., as are known in the art.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant conditions that allow hybridization comparable with that resulting from the use of a DNA probe of at least 40 nucleotides in length, in a buffer containing 0.5 M NaHPO4, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well known by those skilled in the art of molecular biology.

While PCR is the amplification method used in the examples herein, it is understood that any amplification method that uses a primer may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependent amplification (HDA); transcription-mediated amplification (TMA), and the like. Therefore, when the term PCR is used, it should be understood to include other alternative amplification methods. For amplification methods without discrete cycles, reaction time may be used where measurements are made in cycles or Cp, and additional reaction time may be added where additional PCR cycles are added in the embodiments described herein. It is understood that protocols may need to be adjusted accordingly.

Emerging technologies, such as multiplex PCR or MALDI-TOF, are capable of rapidly detecting numerous bacterial and viral pathogens that impact human health. By simultaneously screening for multiple pathogens, these technologies save time and money by reducing the number of laboratory tests required for diagnosis. One challenge with rapid, broad-spectrum yet specific detection is that not all pathogens are present at identical titers. For example, in positive blood cultures Gram-negative bacteria typically grow to higher titers while yeast grows more slowly and to lower titers. This is further complicated by the potential of detecting background environmental organisms. Air, soil, dust, and humans are all carriers of bacterial organisms. Moreover, the test kit itself may contain trace nucleic acids, even if the test kit and its contents have been sterilized. Also, where organisms are cultured, the growth media often contains non-viable organisms, which would not affect culture, but could produce false positives in PCR. If a system is designed uniformly for increased sensitivity to detect low titers pathogens, frequent false positive results may occur from background organisms. Alternatively, if system sensitivity is reduced to avoid background organism detection, low titer organisms may be missed, resulting in false negative detection. Two-step multiplex PCR protocols enable detection over a broad range of titers, but this broad range of detection can make it difficult to distinguish between a true positive and a minor environmental contaminant. By individually tuning the number of PCR cycles performed before detection of each assay, low titer targets can be readily detected in the same multiplex PCR reaction as higher target organisms, while minimizing false positive calls from background contamination, cross-reactivity (which can be problematic in a highly multiplexed reaction), and other extraneous amplification.

Various embodiments disclosed herein use a self-contained nucleic acid analysis pouch to assay a sample for the presence of various biological substances, illustratively antigens and nucleic acid sequences, illustratively in a single closed system. Such systems, including pouches and instruments for use with the pouches, are disclosed in more detail in U.S. Pat. No. 8,394,608; U.S. Patent Application No. 2010-0056383; and WO 2013/074391, herein incorporated by reference. However, it is understood that such pouches are illustrative only, and the multiple PCR reactions discussed herein may be performed in any of a variety of open or closed system sample vessels as are known in the art, including 96-well plates, plates of other configurations, arrays, carousels, and the like, using a variety of amplification systems, as are known in the art. While the term "sample well" is used herein, this term is meant to encompass wells, tubes, and various other reaction containers, as are used in these amplification systems. In one embodiment, the pouch is used to assay for multiple pathogens. Illustratively, various steps may be performed in the optionally disposable pouch, including nucleic acid preparation, primary large volume multiplex PCR, dilution of primary amplification product, and secondary PCR, culminating with optional real-time detection or post-amplification analysis such as melting-curve analysis. Further, it is understood that while the various steps may be performed in pouches of the present invention, one or more of the steps may be omitted for certain uses, and the pouch configuration may be altered accordingly.

Figure 15:
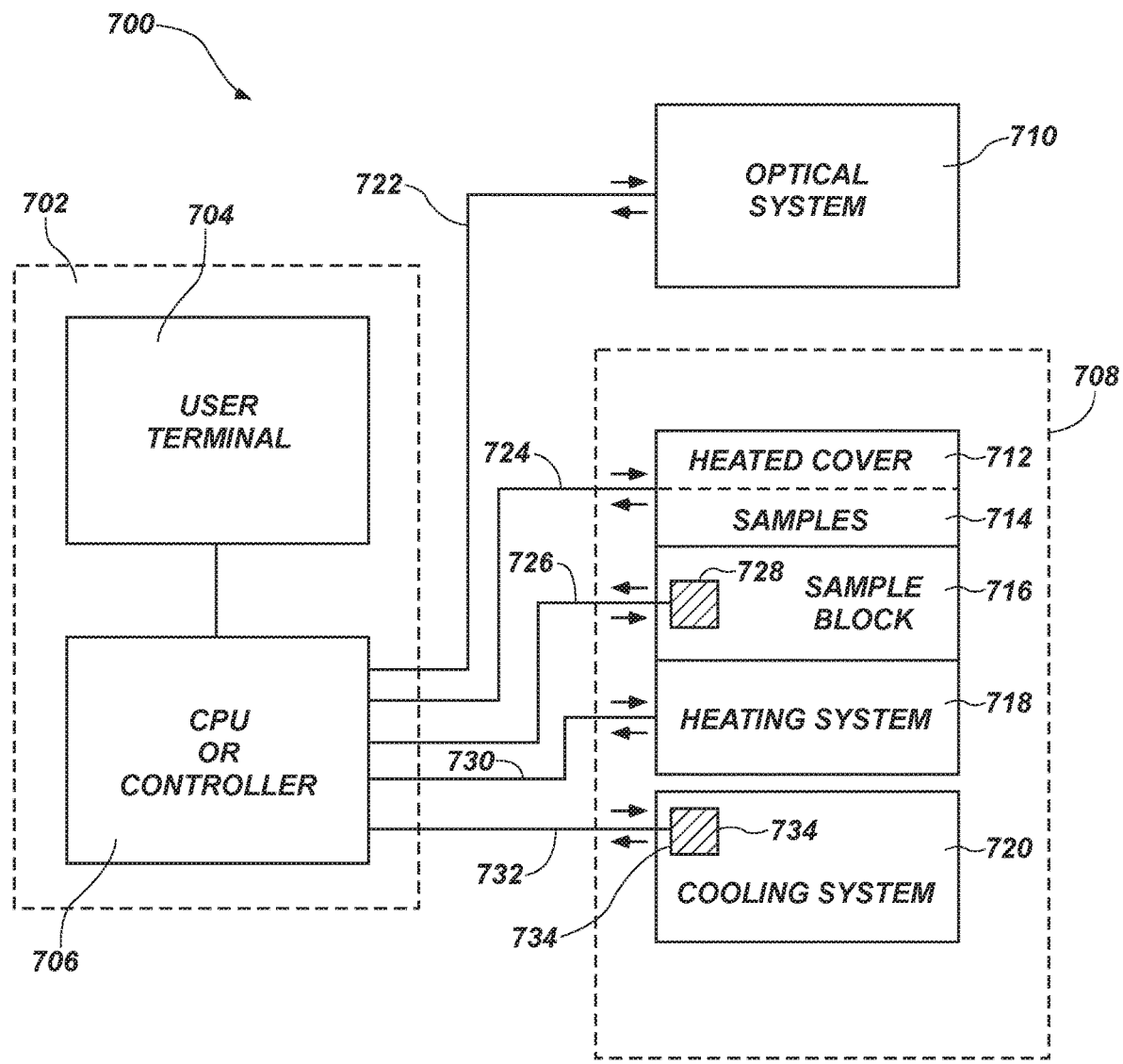
FIG. 15 illustrates a block diagram of an exemplary embodiment of a thermal cycling system in accordance with aspects of the disclosure.

FIG. 1 shows an illustrative pouch 510 for use with the current invention. Pouch 510 is similar to FIG. 15 of U.S. Patent Application No. 2010-0056383, already incorporated by reference, with like items numbered the same. Fitment 590 is provided with entry channels 515a through 515l, which also serve as reagent reservoirs. Illustratively, reagents may be freeze dried in fitment 590 and rehydrated prior to use. Blisters 522, 544, 546, 548, 564, and 566, with their respective channels 538, 543, 552, 553, 562, and 565 are similar to blisters of the same number of FIG. 15 of U.S. Patent Application No. 2010-0056383. Second-stage reaction zone 580 of FIG. 1 is similar to that of U.S. Patent Application No. 2010-0056383, but the second-stage wells 582 of high density array 581 are arranged in a somewhat different pattern. The more circular pattern of high density array 581 of FIG. 1 eliminates corners and can result in more uniform filling of second-stage wells 582. As shown, the high density array 581 is provided with 102 second-stage wells 582. Pouch 510 is suitable for use in the FilmArray instrument. However, it is understood that the pouch embodiment is illustrative only.

Pouch 510 may be used in a manner similar to that described in U.S. Patent Application No. 2010-0056383. A 300 μl mixture comprising the sample to be tested (100 μl) and lysis buffer (200 μl) is injected into injection port (not shown) in fitment 590 near entry channel 515a, and the sample mixture is drawn into entry channel 515a. Water is also injected into a second injection port (not shown) of the fitment 590 adjacent entry channel 515l, and is distributed via a channel (not shown) provided in fitment 590, thereby hydrating up to eleven different reagents, each of which were previously provided in dry form at entry channels 515b through 515l via. These reagents illustratively may include freeze-dried PCR reagents, DNA extraction reagents, wash solutions, immunoassay reagents, or other chemical entities. Illustratively, the reagents are for nucleic acid extraction, first-stage multiplex PCR, dilution of the multiplex reaction, and preparation of second-stage PCR reagents, as well as control reactions. In the embodiment shown in FIG. 1, all that need be injected is the sample solution in one injection port and water in the other injection port. After injection, the two injection ports may be sealed. For more information on various configurations of pouch 510 and fitment 590, see U.S. Patent Application No. 2010-0056383, already incorporated by reference.

After injection, the sample is moved from injection channel 515a to lysis blister 522 via channel 514. Lysis blister 522 is provided with ceramic beads and is configured for vortexing via impaction using rotating blades or paddles provided within the FilmArray instrument. Once the cells have been adequately lysed, the sample is moved through channel 538, blister 544, and channel 543, to blister 546, where the sample is mixed with nucleic acid-binding magnetic beads. The mixture is allowed to incubate for an appropriate length of time, illustratively approximately 10 seconds to 10 minutes. A retractable magnet located within the FilmArray instrument adjacent blister 546 captures the magnetic beads from the solution, forming a pellet against the interior surface of blister 546. The liquid is then moved out of blister 546 and back through blister 544 and into blister 522, which is now used as a waste receptacle. One or more wash buffers from one or more of injection channels 515c to 515e are provided via blister 544 and channel 543 to blister 546. Optionally, the magnet is retracted and the magnetic beads are washed by moving the beads back and forth from blisters 544 and 546 via channel 543. Once the magnetic beads are washed, the magnetic beads are recaptured in blister 546 by activation of the magnet, and the wash solution is then moved to blister 522. This process may be repeated as necessary to wash the lysis buffer and sample debris from the nucleic acid-binding magnetic beads.

After washing, elution buffer stored at injection channel 515f is moved to blister 548, and the magnet is retracted. The solution is cycled between blisters 546 and 548 via channel 552, breaking up the pellet of magnetic beads in blister 546 and allowing the captured nucleic acids to dissociate from the beads and come into solution. The magnet is once again activated, capturing the magnetic beads in blister 546, and the eluted nucleic acid solution is moved into blister 548.

First-stage PCR master mix from injection channel 515g is mixed with the nucleic acid sample in blister 548. Optionally, the mixture is mixed by forcing the mixture between 548 and 564 via channel 553. After several cycles of mixing, the solution is contained in blister 564, where a pellet of first-stage PCR primers is provided, at least one set of primers for each target organism, and first-stage multiplex PCR is performed. If RNA targets are present, an RT step may be performed prior to or simultaneously with the first-stage multiplex PCR. First-stage multiplex PCR temperature cycling in the FilmArray instrument is illustratively performed for 15-20 cycles, although other levels of amplification may be desirable, depending on the requirements of the specific application.

After first-stage PCR has proceeded for the desired number of cycles, the sample may be diluted, illustratively by forcing most of the sample back into blister 548, leaving only a small amount in blister 564, and adding second-stage PCR master mix from injection channel 515i. Alternatively, a dilution buffer from 515i may be moved to blister 566 then mixed with the amplified sample in blister 564 by moving the fluids back and forth between blisters 564 and 566. If desired, dilution may be repeated several times, using dilution buffer from injection channels 515j and 515k, and then adding second-stage PCR master mix from injection channel 515h to some or all of the diluted amplified sample. It is understood that the level of dilution may be adjusted by altering the number of dilution steps or by altering the percentage of the sample discarded prior to mixing with the dilution buffer or second-stage PCR master mix comprising components for amplification, illustratively a polymerase, dNTPs, and a suitable buffer, although other components may be suitable, particularly for non-PCR amplification methods. If desired, this mixture of the sample and second-stage PCR master mix may be pre-heated in blister 564 prior to movement to second-stage wells 582 for second-stage amplification. Such preheating may obviate the need for a hot-start component (antibody, chemical, or otherwise) in the second-stage PCR mixture.

The illustrative second-stage PCR master mix is incomplete, lacking primer pairs, and each of the 102 second-stage wells 582 is pre-loaded with a specific PCR primer pair. If desired, second-stage PCR master mix may lack other reaction components, and these components may be pre-loaded in the second-stage wells 582 as well. Each primer pair may be similar to or identical to a first-stage PCR primer pair or may be nested within the first-stage primer pair. Movement of the sample from blister 564 to the second-stage wells 582 completes the PCR reaction mixture. Once high density array 581 is filled, the individual second-stage reactions are sealed in their respective second-stage blisters by any number of means, as is known in the art. Illustrative ways of filling and sealing the high density array 581 without cross-contamination are discussed in U.S. Patent Application No. 2010-0056383. Illustratively, the various reactions in wells 582 of high density array 581 are simultaneously thermal cycled, illustratively with one or more peltier devices, although other means for thermal cycling are known in the art.

The illustrative second-stage PCR master mix contains the dsDNA binding dye LCGreen® Plus to generate a signal indicative of amplification. However, it is understood that this dye is illustrative only, and that other signals may be used, including other dsDNA binding dyes, and probes that are labeled fluorescently, radioactively, chemiluminescently, enzymatically, or the like, as are known in the art.

The illustrative FilmArray instrument is programmed to make positive or negative calls for each second-stage reaction based on a post-PCR melt. The melt curve must produce a melt peak (first derivative maximum or negative first derivative maximum) within a pre-defined temperature range, for the call to be positive. It is understood that this method of calling each second-stage reaction is illustrative only, and that calls could be made using real-time amplification data or by other means, as are known in the art.

Example 1

The FilmArray Blood Culture Identification (BCID) system is designed to provide rapid identification of a broad range of microorganism pathogens directly from blood culture. The illustrative BCID panel detects the most common bacteria and yeast isolated from positive aerobic blood cultures (PABC), as well as select antibiotic resistance genes, with ≥95% sensitivity. A commercial BCID panel is available from BioFire Diagnostics, Inc. This example uses a research version of the FilmArray BCID panel to demonstrate methods of distinguishing between true positives and environmental contamination.

Various gram-positive and gram-negative bacteria, as well as *Candida* yeast isolates were tested for assay reactivity. Mock PABC samples were prepared by spiking microorganism into a mixture of human whole blood and BD BACTEC Aerobic Plus/F blood culture medium. Microorganisms were spiked at concentrations consistent with that observed for blood culture bottles that had recently been indicated 'positive' for growth by the BD BACTEC 9050 system (103 to 108 CFU/mL)(Becton Dickinson, Franklin Lakes, N.J.). Exclusivity samples were prepared at microorganism concentrations expected for blood culture bottles that may have remained overnight (~8 hours after the initial positive signal) in a blood culture machine (108 CFU/mL yeast and 1010 CFU/mL for bacteria). Samples were loaded into a FilmArray BCID pouch and processed in a FilmArray instrument. Nucleic acid extraction, purification, amplification, and results analysis are automated using the FilmArray system, with a total processing time of approximately one hour.

PABC samples from children and adults from three different sites were tested in a FilmArray BCID pouch. FilmArray results were compared to conventional blood culture and susceptibility testing. One 250 µl aliquot from each PABC was mixed with 500 µl lysis buffer, and 300 µl of this mixture was loaded into a pouch per instructions and tested for gram positive and gram negative bacteria, fungi and antibiotic resistance genes.

Within the FilmArray instrument, subsequent to sample prep, the first-stage multiplex PCR mixture was thermocycled in blister 564 from 60° C. for 25 seconds to 96° C. for 4 seconds for 20 cycles. After first-stage PCR was complete, the mixture was diluted and was transferred to each of the second-stage wells 582. The second-stage PCR reactions were subjected to 63° C. for 19 seconds to 94° C. for 0 seconds for an additional 32 cycles. Melts in this illustrative example were performed after cycles 20, 26, and 32 for each second-stage reaction well 582 to generate melt curves, and each well was called positive if the melt curve showed a melt peak (negative first derivative of the melt curve) in the pre-defined temperature range for each second-stage assay. It is noted that other cycles may be used for melt analysis, with 20, 26, and 32 cycles being illustrative only, and each assay may have its own pre-defined temperature range that is related to the Tm of the expected amplicon. The pre-defined temperature range works to exclude amplified products that are non-specific such as primer-dimers, which often will have a significantly different Tm. For organisms with variability in the target sequence, it may be desirable to have a wider pre-defined range, as sequence variability may result in slightly different Tms. For organisms with highly conserved target sequences, it may be desirable to have a narrower pre-defined temperature range, thus excluding most non-specific and cross-reactive amplification.

FIGS. 2A-B show illustrative amplification and melting results for an *A. baumannii* test. FIG. 2A shows results for a contaminant that could lead to a false positive call, while FIG. 2B shows the results for a true positive that was run after blood culture, as discussed above. It is noted that each assay is run in triplicate in high density array 581 in the illustrative BCID panel, and two of the three wells 582 must show a positive result for the system to call that organism positive. In FIG. 2A, in two of the three replicates the amplification curve shows a crossing point ("Cp") of 29.2. Thus, a call made before cycle 29, illustratively at cycles 20 or 26, would be negative, but a call made after cycle 29, illustratively at cycle 32, would be positive. This is confirmed in the melts, where there is no melt peak after cycles 20 (melt 1) and 26 (melt 2), but there is a clear melt peak after cycle 32 (melt 3) for all three replicates, using a pre-defined temperature range of 78-83° C. Using either the amplification curve or the melt peaks, with the illustrative 20 or 26 second-stage amplification cycles, this assay properly could have been called negative, but if PCR had gone through the illustrative 32 cycles, this assay could have resulted in a false positive. In FIG. 2B, it is seen that the true positive amplified much earlier with a Cp between 7.9 and 8.0 for each well, and melt peaks at all three illustrative cycles would be called positive.

From FIGS. 2A-B, one may consider terminating the second-stage amplification at a cycle no later than cycle 26. Indeed, if *A. baumannii* were the only organism assayed, such would be a good strategy. However, a number of organisms in the BCID panel and in other panels amplify much later, illustratively because of slower growth in culture, less efficient PCR, or because there are fewer copies of the target sequence in a positive blood culture. Fewer copies of the target sequence may be present because the organism is capable of triggering a positive blood culture with fewer cells, or because there may be only one copy of the target sequence per cell, as compared to plasmid or RNA sequences that may be present in significantly higher copy numbers.

FIGS. 3A-B show illustrative amplification and melting results for a *C. tropicalis* assay. With this organism, true positives often do not show up until after cycle 26. With *C. tropicalis*, false positives would be rare, but false negatives would be common if second-stage PCR were terminated significantly earlier than cycle 32. If a single second-stage cycle were chosen for all assays, there would be either a risk of false positives for the assays that tend to have an earlier Cp (such as *A. baumannii*) or a risk of false negatives for assays that tend to have a later Cp (such as *C. tropicalis*), or both if a compromise cycle were chosen. Using different cycles for the calls for each of these organisms improves the overall accuracy of the assay.

Figure 4A:
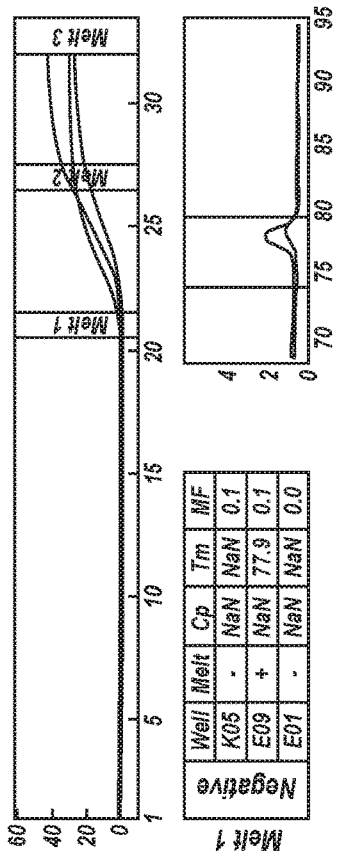
FIGS. 4A-B show amplification and melt curves after three different cycles for *S. aureus*.
Figure 4B:
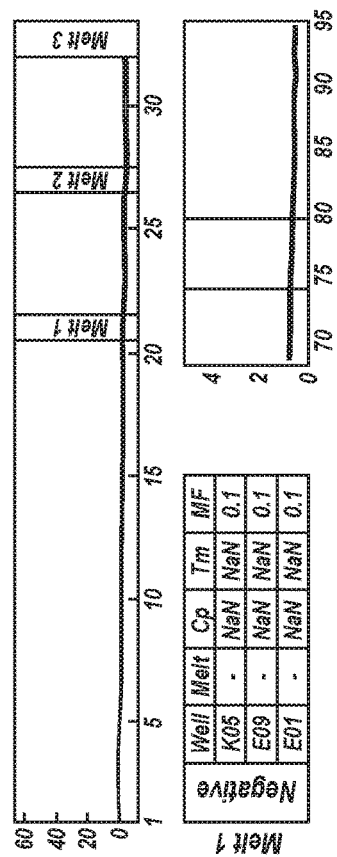

FIGS. 4A-B show the amplification and melting results for an *S. aureus* assay.

With this organism in the FilmArray BCID panel, true positives sometimes show up as early as cycle 20. FIG. 4B shows that all three replicates were called negative after 20 cycles by Cp, but one replicate was called positive by melt. However, all three replicates were called positive after 26 cycles by Cp and melt. While the true negative shown in FIG. 4A did not show any amplification, even after 32 cycles, it is known that *S. aureus* is a moderate contamination risk. Accordingly, while choosing cycle 32 may be acceptable based on the data shown in FIGS. 4A-B, cycle 26 is also a viable choice, with less risk of false positives from environmental contamination.

Each organism in the illustrative BCID panel was analyzed to determine whether melt cycle 1 (second-stage PCR cycle 20), melt cycle 2 (second-stage PCR cycle 26), or melt cycle 3 (second-stage PCR cycle 32) would be most appropriate to use to minimize both false positives and false negatives. The organisms were assigned as follows in Table 1:

TABLE 1

| Melt Cycle 1 (Cycle 20) | Melt Cycle 2 (Cycle 26) | Melt Cycle 3 (Cycle 32) |
|---|---|---|
| A. baumannii | Enterococcus | K. pneumoniae | C. albicans |
| E. coli | L. monocytogenes | K. oxytoca | C. glabrata |
| E. cloacae | Staphylococcus | S. marcescens | C. krusei |
| Enterobacteriaceae | S. aureus | P. aeruginosa | C. parapsilosis |
| Proteus | Streptococcus | N. meningitidis | C. tropicalis |
| | S. agalactiae | mecA | |
| | S. pneumoniae | KPC | |
| | S. pyogenes | vanA/B | |
| | H. influenzae | | |

In the illustrative embodiment, the FilmArray instrument was programmed to collect the melt result for each organism only in the melt cycle listed above. While only the melt cycle identified in Table 1 was used for each organism, it is understood that obtaining amplification or melt peak information over multiple cycles for a single well may be useful in some circumstances.

In general, melt cycle 1 targets are present at the highest titers in positive aerobic blood cultures, but also present as background organisms and are the highest risk for unexpected positives. Melt cycle 2 targets present at high titers in positive aerobic blood cultures, but have a low presence as background organisms and are a medium risk for unexpected positives. Melt cycle 3 targets present at low titers in positive aerobic blood cultures, but also have low to no presence as background organisms and have a low risk for unexpected positives.

When the three melts discussed above were used, it was found that the illustrative version of the FilmArray BCID panel exhibited 100% reactivity (111/111) with the panel of inclusivity microorganisms (including those harboring antimicrobial resistance genes). For example, the illustrative FilmArray BCID panel detected 17/17 *Staphylococcus* isolates, 19/19 *Enterococcus* isolates, and 30/30 Enterobacteriaceae isolates. Similarly, the illustrative FilmArray BCID system did not detect 62/62 (100%) microorganisms for which the assays were not expected to react. The average specificity per interpretation [True Negative/(True Negative+False Positive)] in the BCID system was 100% (155/155; 95% CI 98.1-100.0%). These results demonstrate that each well may be called correctly using only a single melt cycle for that reaction, which may be different than the single melt cycle used for the reaction in another well in the same assay.

While three melt cycles were used in this example, it is understood that any number of melt cycles may be used and that any cycle may be chosen as a melt cycle. Separation between false positives and false negatives may be achieved with only two melt cycles in some assays, whereas four or more melt cycles may be needed in other assays. Further, while the example used samples from culture, it is understood that multiple melt cycles may be appropriate for assays using uncultured materials. Further, while melting is used in this example, amplification curves with cut-offs or Cps at the various cycles may be used to determine whether the sample is positive for the target.

Additionally, it is understood that the information obtained for one organism can be used to assist with positive or negative calls for other organisms, particularly if there is some cross-reactivity between the organisms, or if there is some other relationship such as a bacterium and an antibiotic resistance gene associated with that bacterium. In the above example, *Enterococcus* ("Entero") and *Staphylococcus* ("Staph") are both detected in melt cycle 2. However, in many known assays for Entero, due to similarities in target sequence, there is cross-reactivity with Staph, thereby potentially causing a late Cp in a true negative Entero sample that is positive for Staph. To reduce the effect of potential cross-reactivity for the Entero assay in such a situation where cross-reactivity is an issue, a positive or negative call for Staph may be made, illustratively using melt cycle 2 (cycle 26). If Staph is positive, thereby affecting the Entero sample, Entero could be called based on an earlier result, illustratively melt cycle 1 (cycle 20). If Staph is negative, then the Entero assay would be unaffected and the call may be made illustratively at melt cycle 2, or whichever cycle was chosen as optimized for that assay without cross-reactivity. It is noted, however, that in blood culture, a positive bottle ring is based on the combined organism growth of all organisms that are present, and one or more organisms may be present at amounts lower than either would be from a single infection. The cycle at which the cross-reactive assay is called may need to be adjusted accordingly. By adjusting the cycle used for the call of the cross-reactive assay based on a positive or negative call from the other assay, cross-reactivity issues from double infection samples can be called accurately, illustratively without the need to redesign the primers to avoid cross-amplification.

It is understood that, while the above example identifies organisms, it is understood that the same methods and devices may be used to identify different target sequences in one or several organisms by amplifying different loci of that organism.

Example 2

In Example 1, melts at different cycle numbers were used to distinguish between environmental contamination and clinical infection, wherein each test in the panel was assigned a cycle number, and positives and negatives were called based on the result at the assigned cycle number. Using different cycle numbers for calls can also be used to distinguish between potential "false positives" where nucleic acid is present at substantial quantities but not clinically relevant and clinically relevant true positives that do not have a crossing point until a later cycle. One such example is with latent viral infection through chromosomal integration, wherein the chromosomally integrated viral DNA may or may not be responsible for the clinical symptoms.

For example, an individual may have inherited the HHV6 virus from a parent who had been infected with the virus and the virus was latently chromosomally integrated (termed chromosomally-integrated HHV6, "ciHHV6"). This individual would have some or all of the HHV6 virus integrated in essentially every nucleated cell, and a PCR test for HHV6 would always come up positive, even if the individual has a latent infection with no active clinical symptoms from that virus. For such a patient with no active symptoms from that virus, the integrated viral chromosome would not be clinically relevant, and any symptoms would be from some other source.

For HHV6 patients who have an active case of meningitis and do not have ciHHV6 virus (hereinafter "clinically-relevant infection"), it is expected that a FilmArray second-stage crossing point from a spinal fluid sample would be around cycle 25-30, while a meningitis patient having a latent ciHHV6 virus would have a FilmArray second-stage crossing point around cycle 6-10. In such a situation, the first melt cycle could be illustratively around cycle 10, and a later melt cycle could be done illustratively around cycle 30. However, it is understood that these cycles are illustrative only and other cycles may be appropriate. If the first melt cycle were positive, the test may report a "negative", or it may report a "chromosomal integration" or some other result indicative of the early cycle positive result. Of course, if the first melt cycle were positive, the later melt cycle would also be positive. However, if the first melt cycle were negative and the second melt cycle were positive, this would be an indication of current infection, and a "positive" result would be reported. Thus, in some cases, an early cycle "positive" can be used to identify a non-clinically relevant positive result.

Example 3

In Examples 1 and 2, different cycle numbers were used to distinguish between environmental contamination, potentially non-clinically relevant infection, and clinically-relevant infection. In this example, additional cycles are used to enable detection of low level true positives. In this method, the detection and identification method is a modified two-step process. The first step is a set amplification protocol, optionally with additional melt cycles as used in Examples 1 and 2, and the second step employs a higher signal-to-noise detection during at least one subsequent melt. An illustrative protocol is shown in FIG. 5.

Figure 5:
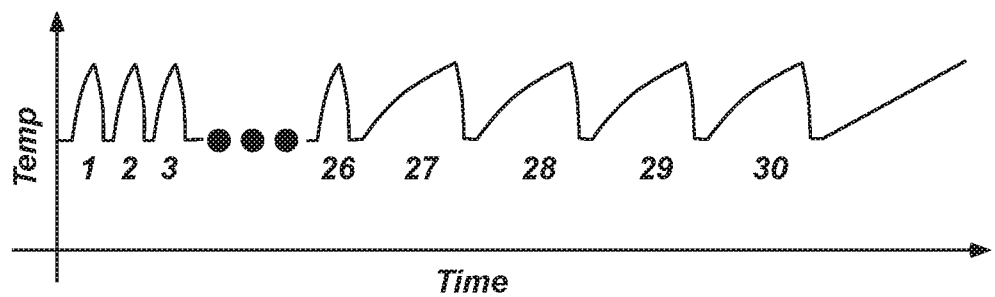
FIG. 5 shows an illustrative cycling protocol for detecting low load samples.
Figure 6:
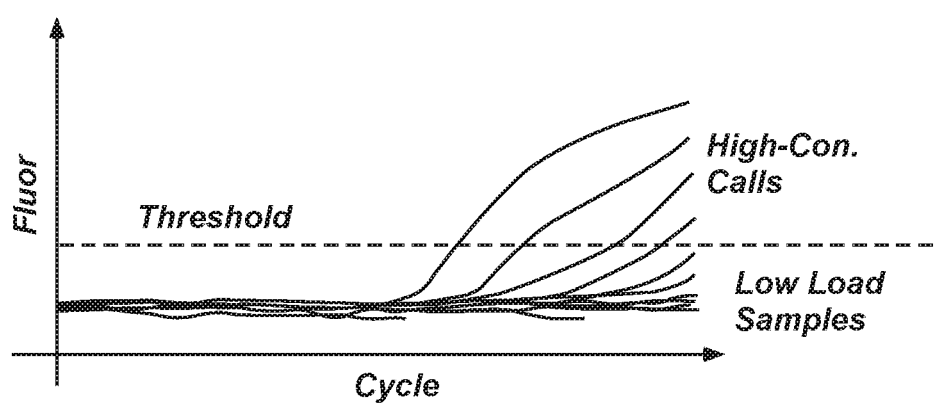
FIG. 6 shows illustrative amplification curves and cut-off fluorescent threshold.

As shown in FIG. 5, a set number of amplification cycles, illustratively 26 cycles, are run. Any wells that return a positive result at cycle 26 optionally need not be analyzed further. The positive result may be made by amplification curve, or may be made or confirmed by a melt curve analysis as discussed above, for those samples that show amplification, illustratively by exceeding a threshold fluorescence level as indicated by the High-Con calls in FIG. 6, or other methods as are known in the art. Thereafter, optionally a melt is run during each of a plurality of additional cycles. After each cycle, if a melt peak is detected, the shape of the amplification curve optionally may be analyzed for further confidence of the positive calls. Illustrative methods of making positive calls from the shape of amplification curves may be found in U.S. Pat. Nos. 6,387,621; 6,730,501; and 7,373,253, and U.S. Patent Application No. 2011-0238323, all of which are herein incorporated by reference. Such methods may aid in distinguishing true amplification from signal drift, which is particularly useful with low level positives. After these additional cycles, illustratively after cycle 30, the light source, illustratively an LED although other excitation devices may be used, in the instrument is adjusted to increase the power. After adjusting the LED power, the instrument collects fluorescence data during a melt. This power adjustment is made to increase the signal-to-noise ratio for detecting low load samples. A reason for not going to full power for the initial melt is that this may have the effect of railing the signal from one or more sample wells that were called positive after cycle 26, as these samples already had a significant load. However, data collection from these wells optionally would be terminated after the positive call at cycle 26, so the railing would not have any effect on reported results. Finally, a melt curve analysis (amplification detection as described above and/or and Tm identification) is performed on all reactions with a cycle 26 or cycle 30 end-point fluorescence less than the established threshold, to determine whether any of these sample wells contain a true positive result.

It is understood that the use of cycles 26 and 30 is illustrative only, and that other cycles may be used, as may be desired for the specific application. Furthermore, the additional cycles 27-30 may be omitted, and the light source may be adjusted after the initial amplification.

Example 4

Optionally, instead of or in addition to multiple melting cycles, the light source in the instrument, illustratively an LED, although other excitation devices may be used, may be adjusted for different assays. The data in Table 2 show that if the LED power is reduced, thereby reducing the fluorescence signal, the detection of background bacterial organisms can be reduced. In one illustrative example, reducing the LED power from 70% (approximate current FA setting) to 50% reduced unexpected false positive detection by the FA BCID Enterobacteriaceae test from 90% to 20% of tests after 32 cycles.

TABLE 2

| FA BCID Assay | 10% LED Power | 30% LED Power | 50% LED Power | 70% LED Power | 90% LED Power | Historical Background detection (65% LED Power) |
|---|---|---|---|---|---|---|
| *Abaumannii* | 0/10 (0%) | 1/10 (10%) | 0/10 (0%) | 0/10 (0%) | 0/10 (0%) | 2.17% |
| *Ecloacae* | 0/10 (0%) | 0/10 (0%) | 0/10 (0%) | 0/10 (0%) | 0/10 (0%) | 8.70% |
| *Ecoli* | 0/10 (0%) | 0/10 (0%) | 0/10 (0%) | 4/10 (40%) | 5/10 (50%) | 23.40% |
| Enterobacteriaceae | 0/10 (0%) | 5/10 (50%) | 2/10 (20%) | 9/10 (90%) | 10/10 (10%) | 78.72% |
| mecA | 0/10 (0%) | 0/10 (0%) | 2/10 (20%) | 0/10 (0%) | 0/10 (0%) | 22.58% |

While an illustrative setting is 70% LED power, a single setting may or may not be appropriate for all assays, and it is understood that the ideal LED power may be different for various assays within an array or panel. For example, an assay that is more susceptible to false positives from environmental contamination may be better off with a lower power setting to reduce sensitivity, while an assay that for which low-level positives are important may benefit from higher LED power. Thus, after the individual positive or negative calls are made, the LED power may be reduced, illustratively by 5%, 10%, 15% or more or any other level, and a melt curve generated. If the melt curve is negative, that assay may be flagged as a potential false positive, or it may be reported as a negative. Alternatively or additionally, the LED power may be increased, illustratively by 5%, 10%, 15% or more or any other level, and assays that were previously called negative may be interrogated, with subsequent melt curves potentially indicated a positive result for a low-level assay.

While LEDs and LED power is discussed herein, it is understood that other illumination sources may be used, including incandescent, fluorescent, and other lamps, and adjustment of the power and concomitant lighting output of such lamps is also within the scope of this invention.

Example 5

Figure 7:
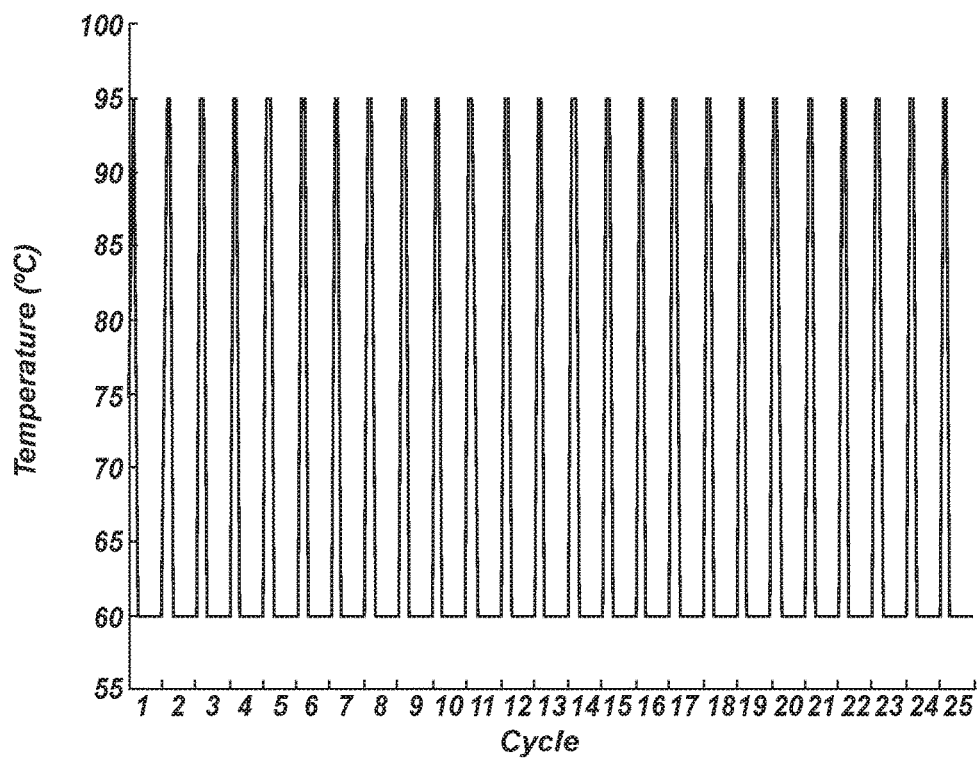
FIG. 7 shows illustrative temperature data that may be collected during a typical two-step PCR protocol. During the denaturation/annealing segment, the temperature is increased from the baseline value to the maximum, followed by a decrease in temperature back to the baseline. During the extension segment, the temperature is held constant.

As an extension of the previous examples, melt curves may be acquired during additional cycles, for example at every cycle or nearly every cycle of PCR, illustratively through continuously acquired temperature and fluorescence data during amplification. For example, an illustrative two-step PCR protocol may be divided two segments: a denaturation/annealing segment where the temperature is constantly changing, and an extension segment where the temperature is held constant. During the denaturation/annealing segment, the temperature of the PCR reaction is increased, illustratively at a constant rate, from a baseline value to a maximum temperature value, followed by a rapid decrease in the temperature back to the baseline value. As the temperature is increased, the dsDNA is separated into two ssDNA fragments. As the temperature is decreased, the PCR primers anneal to the two ssDNA fragments. During the extension segment, the temperature is held constant at the baseline value, allowing the primed ssDNA fragments to extend to form two dsDNA fragments. FIG. 7 is a graphical depiction of this illustrative temperature cycling protocol. However, it is understood that other protocols may be used, wherein the temperature is held constant at any or all of the melting temperature, the annealing temperature, and the elongation temperature, or without any holds. Also, it is understood that the baseline annealing temperature may be the same as or different from the extension temperature.

Figure 8:
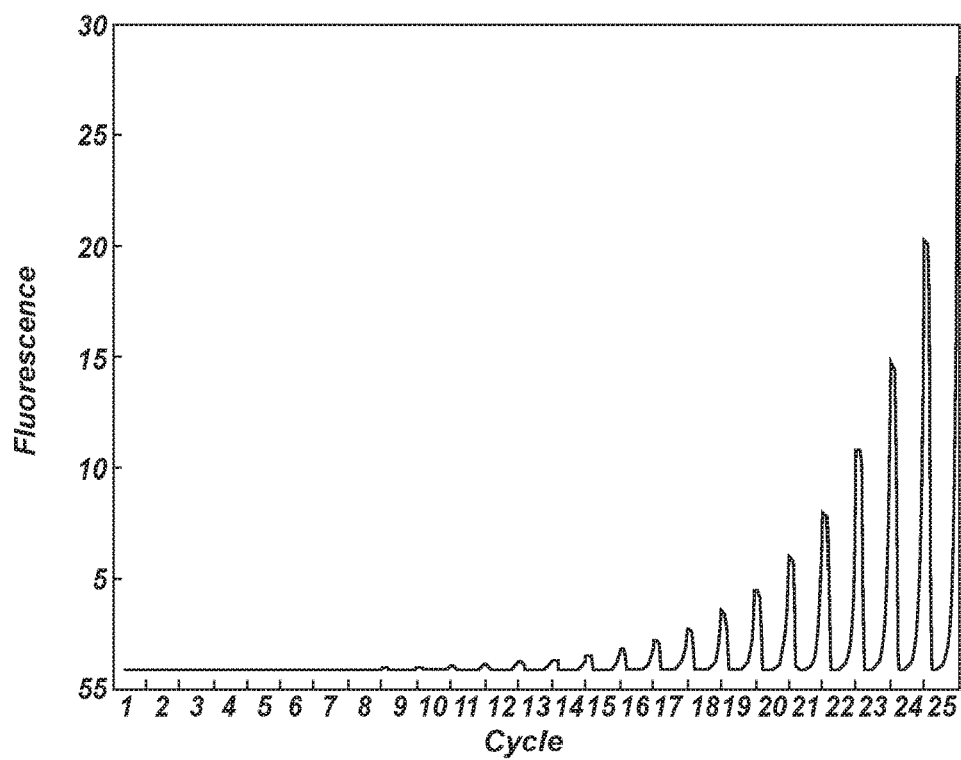
FIG. 8 shows illustrative continuous monitoring of fluorescence data that may be collected during the two-step PCR protocol of FIG. 7.
Figure 9:
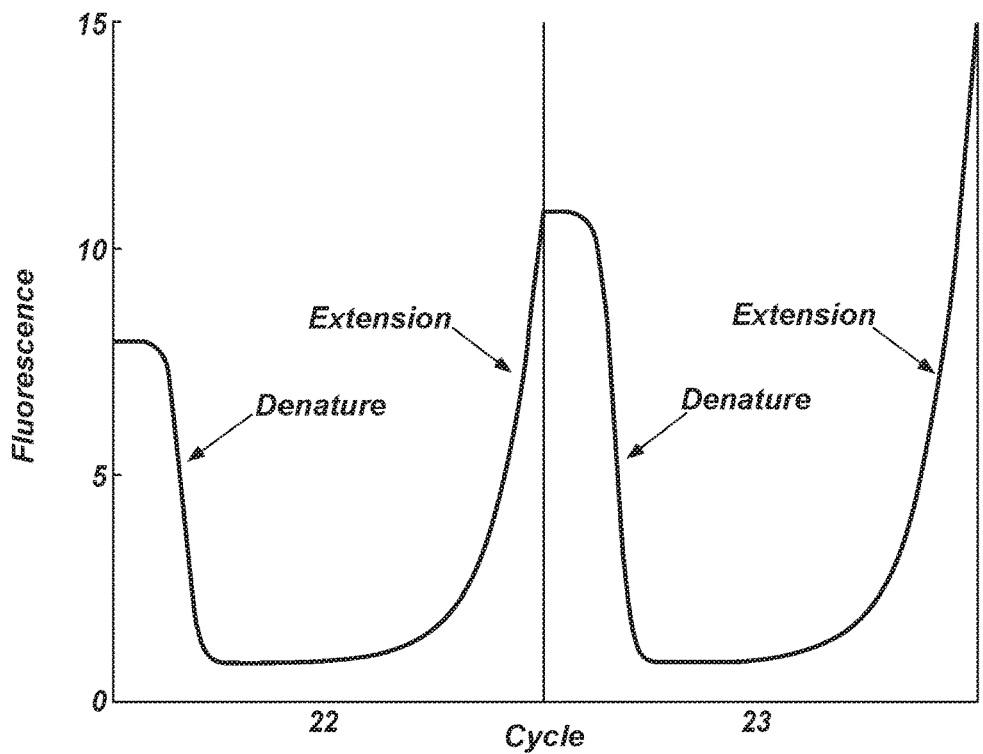
FIG. 9 shows illustrative continuous monitoring of fluorescence data that may be collected during two cycles of a typical two-step PCR protocol. During the denaturation segment, the fluorescence data decreases as the saturating dsDNA-binding dye is released from the dsDNA, resembling a typical melt curve. During the extension segment, the fluorescence data increases as the primed ssDNA fragments are primed and extended into dsDNA fragments.
Figure 10:
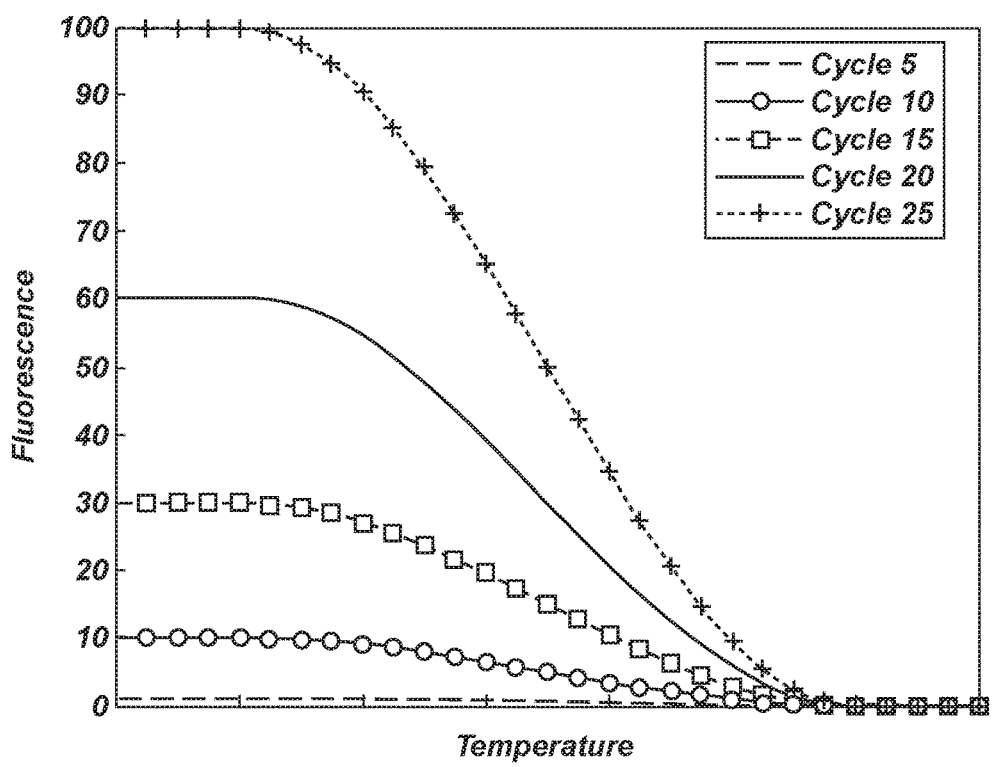
FIG. 10 shows an overlay of illustrative fluorescence data that may be collected during the denaturation segments for several cycles of PCR.

With continuous data acquisition, an instrument may collect temperature and fluorescence data during both segments of the PCR protocol, continuously for all cycles, as shown in FIG. 8. Fluorescence data collected as part of the denaturation segments can be thought of as a series of melt curves. In between each melt curve, the fluorescence data shows amplification as the PCR product is extended and non-specific dsDNA-binding dyes may be used to detect the amplification product (see FIG. 9). At the start of PCR cycling, the amount of dsDNA is low and, therefore, the signal generated during the denaturation segment, is also low. As cycling continues, the amount of PCR product begins to increase. Similarly, the signal generated by the denaturation segment also increases. See FIG. 10 for a graphical depiction of the change to melt curves as PCR cycling progresses.

Figure 11:
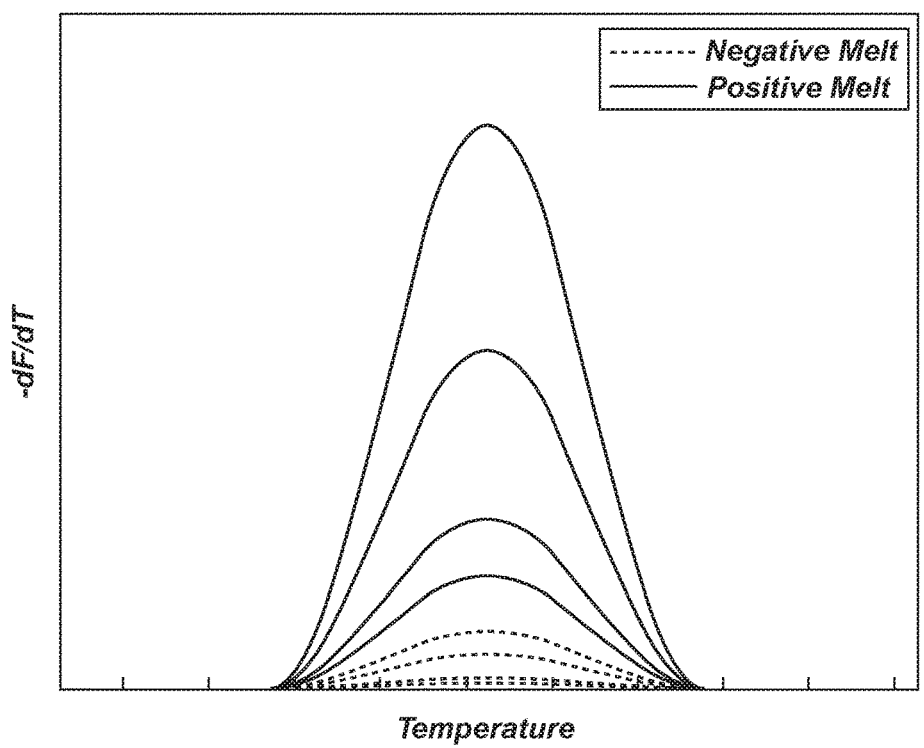
FIG. 11 shows an overlay of illustrative the negative first derivative of the fluorescence data collected during the denaturation segments for several cycles of PCR.

One method for quantifying a target nucleic acid is by determining Cp and comparing the Cp to a standard or to a control. As an alternative to determining Cp by absolute or normalized amplification data, the series of melt curves discussed above may be used. FIG. 11 shows an illustrative set of negative derivative melt curves, wherein the flattest curves represent the earliest cycles and the area under the curve increases through a number of cycles. It is expected that such derivative melt curves acquired at a plurality of cycles during amplification can be used to determine Cp. In this illustrative example, the height of the transition for each melt curve or the area under the negative first derivative of the melt curve can be determined for each cycle. The Cp may then be assigned to the cycle at which this value exceeds a pre-determined threshold. It is understood that every cycle may be used, or fewer than all cycles may be used for an approximate Cp.

Additional methods for determining Cp may be applied. For example, a melt detector may be used (see U.S. Pat. Nos. 6,387,621; 6,730,501; and 7,373,253, herein incorporated by reference). The detector would interrogate curve shape and background noise to determine if PCR product is present in the sample. The use of a melt detector could be used to increase the sensitivity of the system (See Poritz, et al., PLos One 6(10): e26047). Optionally, additional filters could be applied to the melt curve analysis to window the melt transition to increase the specificity of the system, by analyzing only those melt curves having a melting transition, illustratively displayed as a melt peak, within a set temperature range. It is expected that such methods would result in a more accurate Cp.

Example 6

In another illustrative example, methods of continuous monitoring of temperature and fluorescence are used for relative quantification, illustratively using a dsDNA-binding dye in a single reaction with a control nucleic acid. In this example, a multiplexed PCR reaction is provided, containing a control nucleic acid at a known initial concentration and a target nucleic acid at an unknown concentration. Illustratively, primers for amplification of the control nucleic acid are present at the same initial concentration as primers for amplification of the target nucleic acid. In addition, it is desirable if the control nucleic acid is selected such that its melting temperature is sufficiently well separated from the melting temperature of the target nucleic acid, so that melting of each of these nucleic acids is discernable from melting of the other. It is understood that multiple target nucleic acids of unknown concentration may be multiplexed in the reaction, noting that it is desirable that the melt curve for each nucleic acid is distinguishable from the others and from the control nucleic acid.

Figure 12:
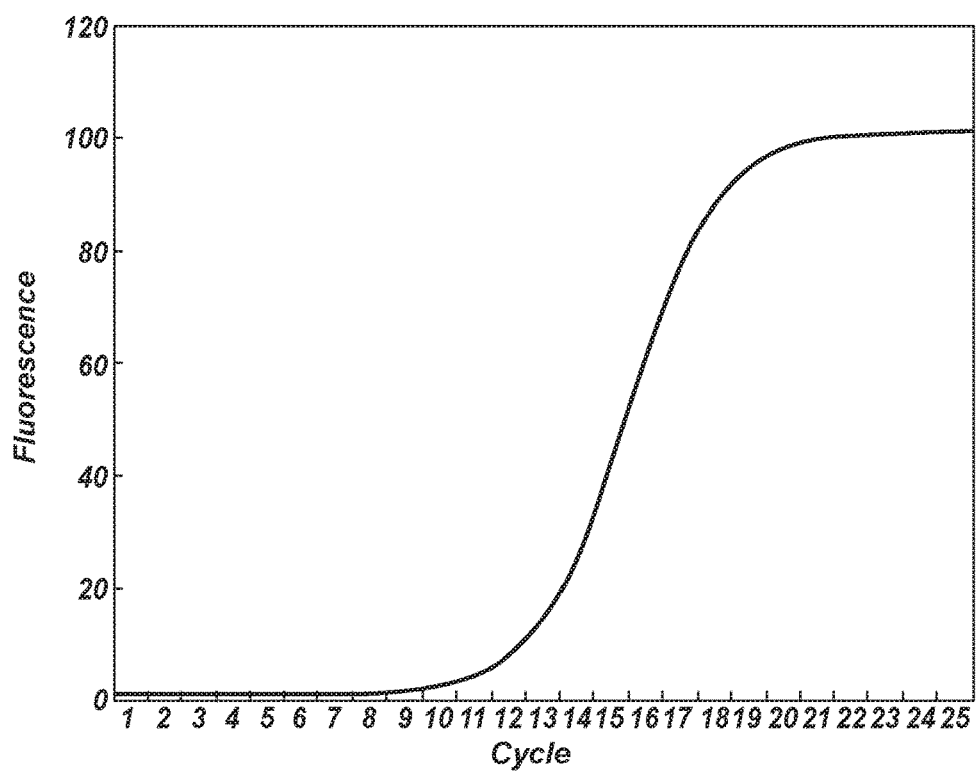
FIG. 12 shows a typical amplification curve for a multiplexed PCR reaction that includes a control nucleic acid and a target nucleic acid of unknown concentration.

In an illustrative PCR application, the amplification of the control nucleic acid and the target nucleic acid produce an amplification curve similar to that shown in FIG. 12. In such a curve generated using a dsDNA binding dye, signal from the control and the target combine to generate a single amplification curve as shown, and information about the amplification of the individual nucleic acids is not discernable.

Figure 13:
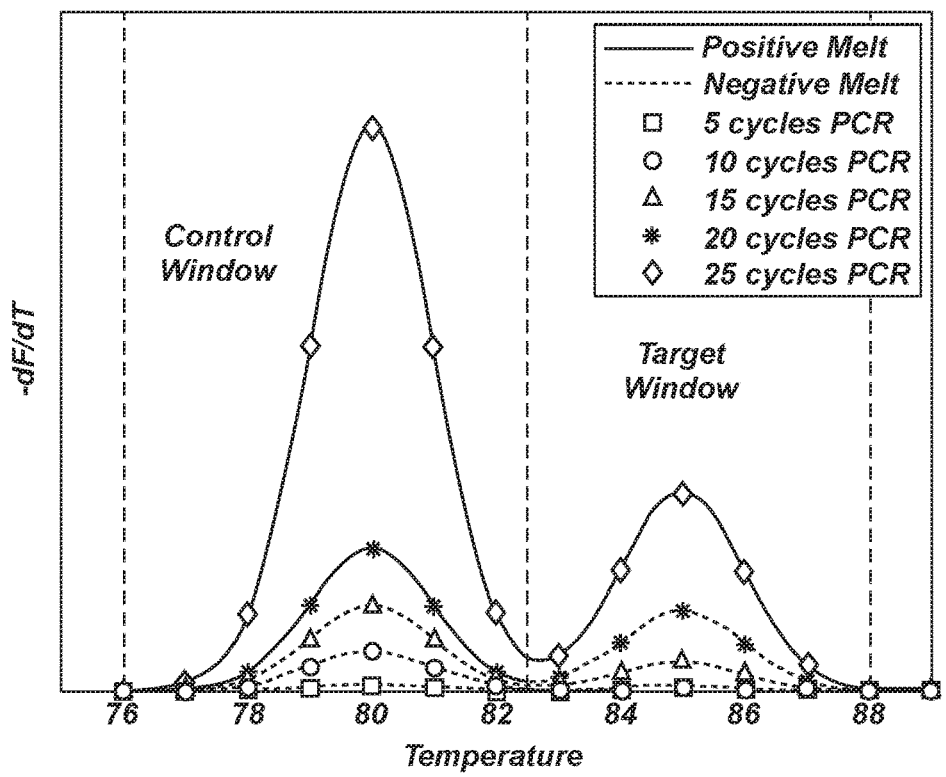
FIG. 13 shows an overlay of illustrative negative first derivative of fluorescence data that may be collected during the denaturation segments for several cycles of PCR of a multiplex reaction containing a control nucleic acid and a target nucleic acid.
Figure 14:
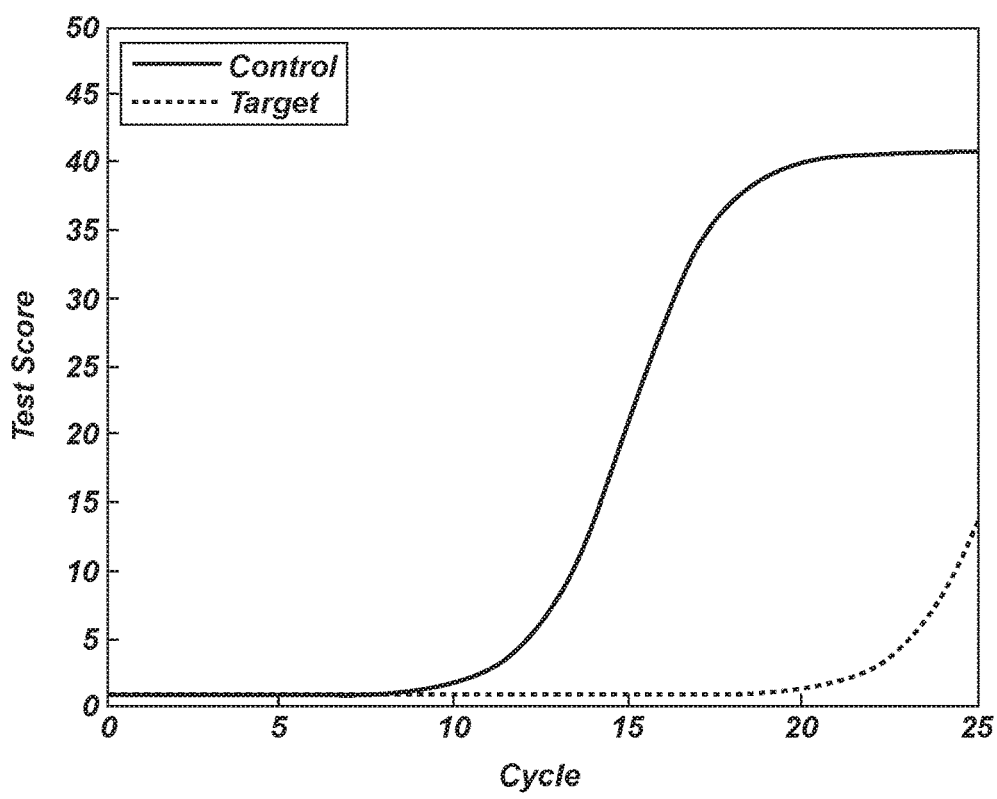
FIG. 14 shows illustrative adjusted real-time PCR curves for the control and sample nucleic acids of FIG. 13. By integrating the negative first derivative of the melt curves generated by continuous monitoring the PCR reaction over the control window, an adjusted amplification curve for the control nucleic acid is generated (solid line). By integrating the negative first derivative of the melt curves generated by continuous monitoring the PCR reaction over the target window, an adjusted amplification curve for the target nucleic acid is generated (dashed line).

With continuous data acquisition, a series of melt curves are generated during PCR cycling. Provided that the melting temperatures of the control nucleic acid and the target nucleic acid are sufficiently separated, the melting profile of each of the two reactions can be distinguished, as shown in FIG. 13. Illustratively, an adjusted amplification curve for the target nucleic acid and optionally for the control nucleic acid can be generated from this series of melt curves. Illustratively, to generate a corrected amplification curve for the control nucleic acid, at each cycle the integral of the negative first derivative of the melt curve over a pre-defined melt window can be computed and plotted as a function of the cycle number, with the Cp determined as the cycle at which each value exceeds a predetermined value. Similarly, a corrected amplification curve for the target nucleic acid may be generated by integrating the negative first derivative of the melt curve over the pre-defined melt window for the target. FIG. 13 shows illustrative negative derivative melt curves for 5, 10, 15, 20, and 25 cycles, with illustrative pre-defined melt windows indicated for the two nucleic acids. Such corrected amplification curves are illustrated in FIG. 14. Other methods for converting the melt curve to a value are known in the art, illustratively using peak height of the negative first derivative. It is understood that the predetermined value should be selected according to method used.

The concentration of the target nucleic acid relative to the control nucleic acid may be computed using the formula:

Relative Concentration=$ET^*Cp,t/EC^*Cp,c$ [Equation 1]

where

ET and EC are the target and control efficiencies, and $Cp,t$ and $Cp,c$ are the target and control crossing points.

The efficiency of the two reactions may be determined empirically and the Cp values for the two reactions may be computed using standard calculations on the amplification curves computed from the series of melt curves, as is known in the art.

Example 7

Certain embodiments of the present invention may also involve or include a PCR system configured to make positive or negative calls from amplification curves or melt curves or a combination thereof. Illustrative examples are described in U.S. Patent Application No. 2010-0056383, already incorporated by reference, for use with pouch 510 or similar embodiments. However, it is understood that the embodiments described in U.S. Patent Application No. 2010-0056383 are illustrative only and other systems may be used according to this disclosure. For example, referring to FIG. 15, a block diagram of an illustrative system 700 that includes control element 702, a thermocycling element 708, and an optical element 710 according to exemplary aspects of the disclosure is shown.

In at least one embodiment, the system may include at least one PCR reaction mixture housed in sample vessel 714. In certain embodiments, the sample vessel 714 may include a PCR reaction mixture configured to permit and/or effect amplification of a template nucleic acid. Certain illustrative embodiments may also include at least one sample block or chamber 716 configured to receive the at least one sample vessel 714. The sample vessel 714 may include any plurality of sample vessels in individual, strip, plate, or other format, and, illustratively, may be provided as or received by a sample block or chamber 716.

One or more embodiments may also include at least one sample temperature controlling device 718 and/or 720 configured to manipulate and/or regulate the temperature of the sample(s). Such a sample temperature controlling device may be configured to raise, lower, and/or maintain the temperature of the sample(s). In one example, sample controlling device 718 is a heating system and sample controlling device 720 is a cooling system. Illustrative sample temperature controlling devices include (but are not limited to) heating and/or cooling blocks, elements, exchangers, coils, radiators, refrigerators, filaments, Peltier devices, forced air blowers, handlers, vents, distributors, compressors, condensers, water baths, ice baths, flames and/or other combustion or combustible forms of heat, hot packs, cold packs, dry ice, dry ice baths, liquid nitrogen, microwave- and/or other wave-emitting devices, means for cooling, means for heating, means for otherwise manipulating the temperature of a sample, and/or any other suitable device configured to raise, lower, and/or maintain the temperature of the sample(s).

The illustrative PCR system 700 also includes an optical system 710 configured to detect an amount of fluorescence emitted by the sample 714 (or a portion or reagent thereof). Such an optical system 710 may include one or more fluorescent channels, as are known in the art, and may simultaneously or individually detect fluorescence from a plurality of samples.

At least one embodiment of the PCR system may further include a CPU 706 programmed or configured to operate, control, execute, or otherwise advance the heating system 718 and cooling system 720 to thermal cycle the PCR reaction mixture, illustratively while optical system 710 collects fluorescent signal. CPU 706 may then generate an amplification curve, a melt curve, or any combination, which may or may not be printed, displayed on a screen, or otherwise outputted. Optionally, a positive, negative, or other call may be outputted based on the amplification and/or melt curve. Optionally only the calls are outputted, illustratively one call for each target tested.

Additional examples of illustrative features, components, elements, and or members of illustrative PCR systems and/or thermal cyclers (thermocyclers) are known in the art and/or described above or in U.S. patent application Ser. No. 13/834,056, the entirety of which is herein incorporated by reference.

Although the invention has been described in detail with reference to preferred embodiments, variations and modifications exist within the scope and spirit of the invention as described and defined in the following claims.

The invention claimed is:

1. A system for detecting which of a plurality of target nucleic acids is in a sample to be screened for multiple targets having titers that comprise higher and lower titers, the system comprising:
 a vessel comprising a plurality of sample wells, each sample well configured for holding a portion of the sample, nucleic acid primers specific for one of the target nucleic acids, a signal producing substance, and components for amplification; and
 an instrument configured to concurrently subject the portion of the sample in each of the plurality of sample wells to amplification conditions and then melting conditions, the instrument comprising a detector for detecting a signal from the signal producing substance indicating amplification,
 wherein the instrument is configured to provide a first number of amplification cycles, then perform a first melt, and output a melting result for the portion of the sample in each of at least some of the plurality of sample wells during or after the first melt, and provide a second number of amplification cycles, then perform a second melt, and output a melting result of the portion of the sample in at least some of the plurality of sample wells during or after the second melt, wherein the instrument is further configured to tune the first number and/or second number of amplification cycles to the titers of the targets.

2. The system of claim 1, wherein the amplification is PCR and the components include a polymerase and dNTPs.

3. The system of claim 1, wherein the first number of amplification cycles before the first melt is different than the second number of amplification cycles before the second melt.

4. The system of claim 1, wherein the signal producing substance is a fluorescent dye.

5. The system of claim 4, wherein the instrument comprises a light source configured to emit optical signal toward the plurality of sample wells during screening of a respective sample, and wherein the instrument is configured to increase power to the light source during the screening of the respective sample.

6. The system of claim 1, wherein the melting result is based on the presence or absence of a melt peak within a predetermined temperature range, and wherein the presence of the melt peak outputs a positive result and the absence of the melt peak outputs a negative result.

7. A system for detecting which of a plurality of target nucleic acids is in a sample, comprising:
 a vessel comprising a plurality of sample wells, each sample well configured for holding a portion of the sample, nucleic acid primers specific for one of the target nucleic acids, a signal producing substance, and components for amplification; and
 an instrument configured for receiving the vessel and for subjecting the vessel to amplification conditions and melting conditions, the instrument further comprising a detector in communication with the plurality of sample wells,
 wherein the instrument is programmed to subject the portion of the sample in each of the plurality of sample wells to amplification conditions through a first number of amplification cycles, direct the detector to perform a first melt detection, and output a first melt detection result for each of the plurality of sample wells after the first number of amplification cycles, and to subject the portion of the sample in each of the plurality of sample wells to amplification conditions through a second number of amplification cycles, direct the director to perform a second melt detection, and output a second melt detection result for each of at least some of the plurality of sample wells after the second number of amplification cycles, wherein the first number of amplification cycles performed before the first melt detection and the second number of amplification cycles performed before the second melt detection are tuned to different titers of different target nucleic acids.

8. The system of claim 7, wherein the nucleic acid amplification is PCR and the components include a polymerase and dNTPs.

9. The system of claim 7, wherein the first number of amplification cycles is a specific number of cycles, and the second number of amplification cycles is an additional specific number of cycles.

10. The system of claim 7, wherein the signal producing substance is a fluorescent dye.

11. The system of claim 10, wherein the instrument comprises a light source configured to emit optical signal toward the plurality of sample wells, and wherein the instrument is configured to increase power to the light source thereby facilitating detection of the targets of the sample.

12. The system of claim 7, wherein the first and second melt detection result is based on the presence or absence of a melt peak within a predetermined temperature range, wherein the presence of the melt peak outputs a positive result, and the absence of the melt peak outputs a negative result.

13. The system of claim 7, wherein the instrument is programmed to subject the plurality of sample wells to amplification conditions through at least a third number of amplification cycles, then direct the detector to perform at least a third melt detection, and output at least a third melt detection result for each of at least some of the plurality of sample wells.

14. The system of claim 1, wherein the instrument is configured to subject the plurality of sample wells to amplification conditions through at least a third number of amplification cycles, perform at least a third melt cycle, and output a melting result for each of at least some of the plurality of sample wells, wherein the number of amplification cycles performed before the third melt is tuned to some of the targets.

15. A system for detecting which of a plurality of target nucleic acids is in a sample to be screened for different targets with different titers, the system comprising:
 a vessel comprising a plurality of sample wells, each sample well configured for holding a portion of the sample, nucleic acid primers specific for one of the target nucleic acids, a signal producing substance, and components for amplification; and
 an instrument configured to receive the vessel and controllably provide amplification conditions and melting conditions for the portion of the sample in each of the sample wells; and a detector controlled by the instrument and in communication with the plurality of sample wells, wherein the instrument is configured to subject the plurality of sample wells to the amplification conditions through a first plurality of amplification cycles, then perform a first melt, direct the detector to detect a first melting result of the portion of the sample in at least some of the plurality of sample wells, subject the plurality of sample wells through a second plurality of amplification cycles, then perform a second melt cycle, direct the detector to detect a second melting result of the portion of the sample in at least some of the plurality of sample wells, and wherein the instrument is further configured to define how many amplification cycles are performed for each of the first and second plurality of amplification cycles based on the different titers of the different targets in the sample.

\* \* \* \* \*